United States Patent
Distler et al.

(10) Patent No.: US 7,317,786 B2
(45) Date of Patent: Jan. 8, 2008

(54) COMPUTED TOMOGRAPHY APPARATUS AND BEAM DIAPHRAGM THEREFOR HAVING ABSORBER ELEMENTS SHAPED TO PRODUCE A NON-UNIFORM BEAM PASSAGE OPENING

(75) Inventors: Friedrich Distler, Fürth (DE); Karlheinz Pauli, Neunkirchen (DE); Heinrich Wallschläger, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 246 days.

(21) Appl. No.: 10/529,287

(22) PCT Filed: Sep. 15, 2003

(86) PCT No.: PCT/DE03/03054

§ 371 (c)(1),
(2), (4) Date: Mar. 25, 2005

(87) PCT Pub. No.: WO2004/029991

PCT Pub. Date: Apr. 8, 2004

(65) Prior Publication Data

US 2005/0243422 A1 Nov. 3, 2005

(30) Foreign Application Priority Data

Sep. 26, 2002 (DE) ................................ 102 44 898

(51) Int. Cl.
*G21K 1/04* (2006.01)
(52) U.S. Cl. ........................ 378/150; 378/145; 378/147
(58) Field of Classification Search ................ 378/147, 378/148, 150, 151, 145
See application file for complete search history.

(56) References Cited

U.S. PATENT DOCUMENTS

| | | | |
|---|---|---|---|
| 4,057,342 A | 11/1977 | Allis | |
| 4,691,335 A | 9/1987 | Telorack | |
| 5,237,599 A * | 8/1993 | Gunji et al. | 378/148 |
| 5,257,305 A | 10/1993 | Van Elburg et al. | |
| 5,406,611 A | 4/1995 | Schobert et al. | |
| 5,557,107 A | 9/1996 | Carcreff et al. | |
| 5,644,614 A | 7/1997 | Toth et al. | |
| 6,259,766 B1 | 7/2001 | Cuppen | |
| 6,396,902 B2 | 5/2002 | Tybinkowski et al. | |
| 6,556,657 B1 | 4/2003 | Tybinkowski et al. | |
| 2002/0015474 A1 | 2/2002 | Tybinkowski et al. | |
| 2003/0086534 A1* | 5/2003 | Seufert | 378/150 |

* cited by examiner

*Primary Examiner*—Chih-Cheng G Kao
(74) *Attorney, Agent, or Firm*—Schiff Hardin LLP

(57) ABSTRACT

A gating device to delimit an x-ray beam, has a device housing, first and second absorber elements mounted in the device housing opposite each other, and an adjustment device for moving the absorber elements relative to each other to set a spacing therebetween forming a slit for passage of an x-ray beam therethrough. Each absorber element has an edge shaped to give the slit a slit width that varies in a longitudinal direction of the slit that increases outwardly from a central position toward respectively opposite ends of the slit. Each slit edge has a middle region producing a uniform width of the slit and further regions respectively disposed on opposite sides of the middle region that produce a linearly, longitudinally increasing slit width. The adjustment device produces a parallelogram-like relative movement between the absorber elements.

5 Claims, 5 Drawing Sheets

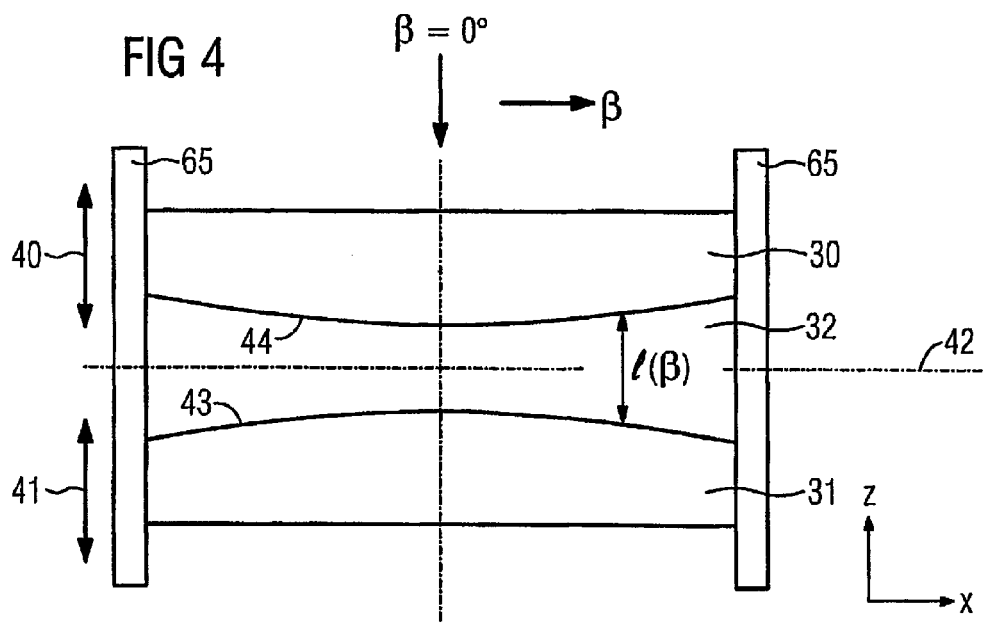
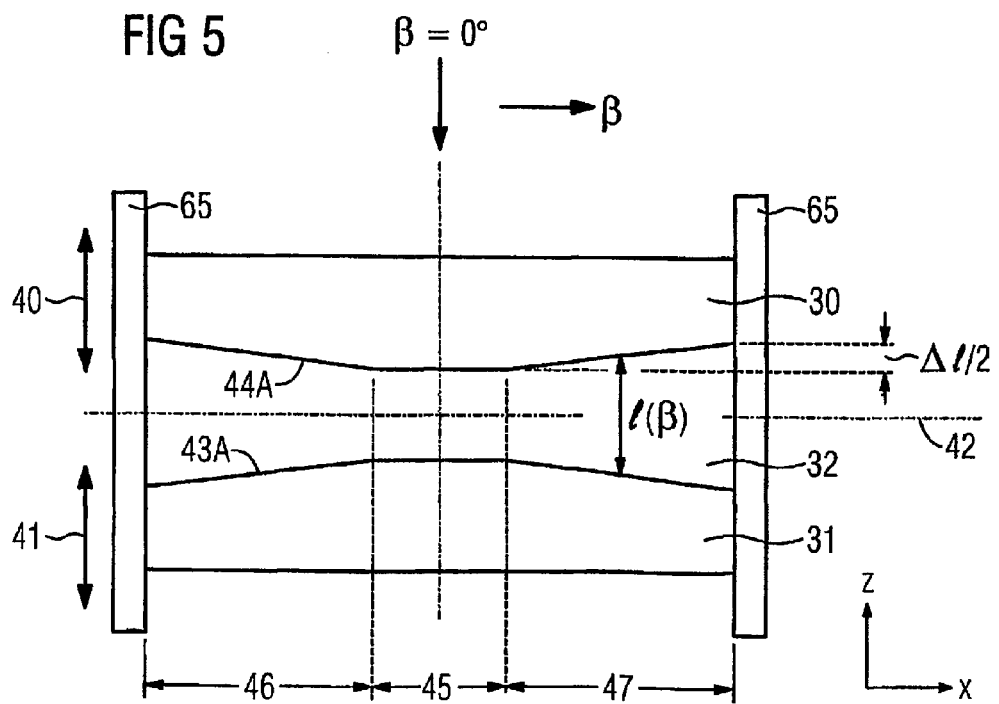

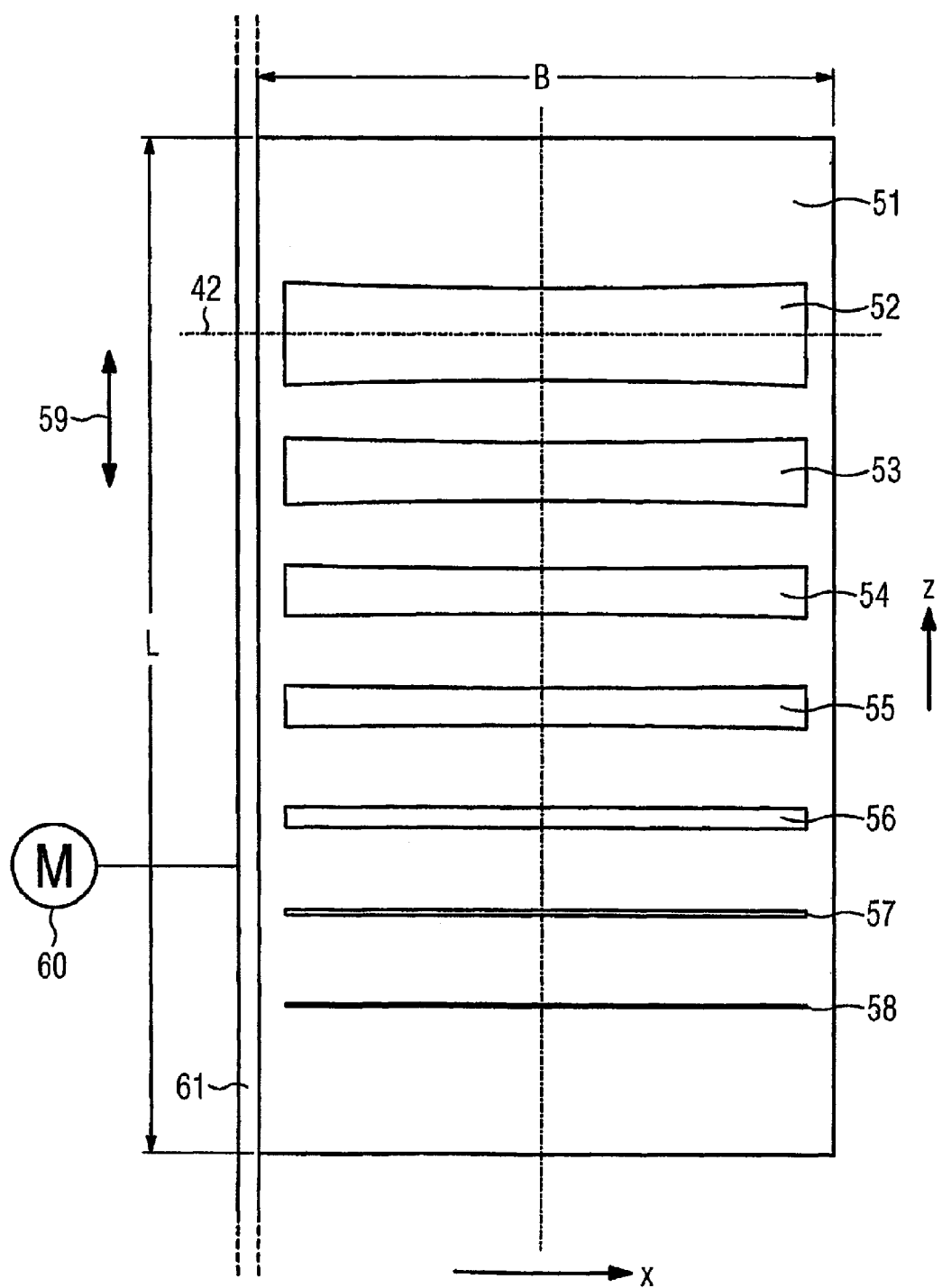

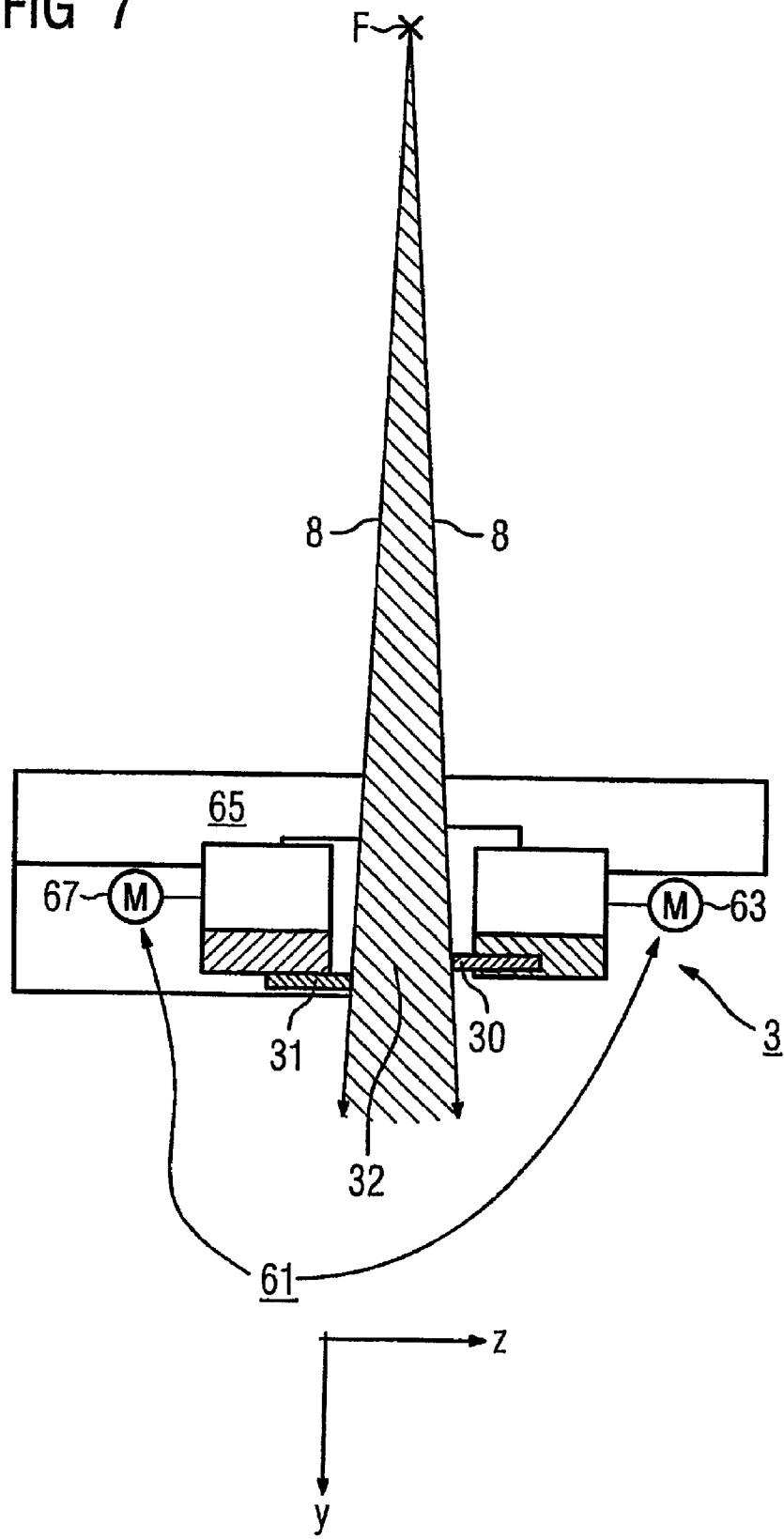

COMPUTED TOMOGRAPHY APPARATUS AND BEAM DIAPHRAGM THEREFOR HAVING ABSORBER ELEMENTS SHAPED TO PRODUCE A NON-UNIFORM BEAM PASSAGE OPENING

BACKGROUND OF THE INVENTION

1. Field of the Invention

The invention concerns a gating device to delimit an x-ray beam, of the type having two absorber elements disposed opposite one another that are adjustable with an adjustment device as to their distance from one another, via which a slit for passage of the x-ray beam can be delimited, wherein the absorber elements are shaped such that the slit exhibits a slit width varying in the slit longitudinal direction, the slit width increasing toward both slit ends starting from a middle position. The invention also concerns a computed tomography apparatus with an x-ray radiator rotatable around a system axis, with an x-ray detector and with a radiator-side gating device.

2. Description of the Prior Art

In an examination of an examination subject or a patient in an x-ray diagnostic apparatus, the examination subject is moved into an x-ray beam emitted by an x-ray source, and the radiation attenuation resulting from this is detected by an x-ray detector. The examination subject is thus located in the beam path between the x-ray receiver and the x-ray detector. The typical x-ray tubes used as x-ray radiators radiate x-ray radiation in a significantly larger solid angle than is necessary for examination at the patient. In order to prevent an unnecessary radiation exposure at the patient, the necessity thus exists to gate out unnecessary x-rays. For this purpose, in conventional x-ray apparatuses it is known to dispose a radiator-side gating device immediately after the x-ray radiator in the beam path, which gating device is also designated as a primary beam diaphragm. For example, such a primary beam diaphragm, with diaphragm plates which can be moved opposite to one another as absorber elements, is known from EP 0 187 245 A1.

In computed tomography apparatuses with multi-row x-ray detectors, a detector-side beam diaphragm (or a beam diaphragm near to the detector) that is mounted in the beam path between the patient and the x-ray detector is also frequently used in addition to a radiator-side gating device that is arranged in the beam path between the x-ray radiator and the patient. It is thereby possible to shade one or more detector rows of the multiple detector rows that are present and to use the remaining detector rows as active detector rows. Since, in a computed tomography apparatus (in particular in such a computed apparatus of the third generation), the x-ray detector rotates around the patient together with the x-ray radiator mounted on a gantry (rotating frame), the control and/or regulation device is normally curved in the azimuthal direction. In adaptation to this geometry, in particular in order to realize a constant separation, a detector-side diaphragm disclosed in DE 42 26 861 C2 for a computed apparatus is fashioned with arc-shaped diaphragm plates.

It is intended that the radiator-side diaphragm only passes such rays that can actually be detected by the x-ray detector (and in particular by its active detector rows). Other x-rays would only unnecessarily penetrate the patient and unnecessarily increase the radiation exposure. Since the multi-row x-ray detector arrays in computed tomography apparatuses are normally equipped with orthogonal rows and columns of detector elements, with regard to the primary beam diaphragm the object is to gate an exactly rectangular ray beam. In other words the resulting slice profile should assume the desired shape and half-width value. Given conventional flat or planar diaphragm plates or absorber elements, this is not perfectly possible due to different separations of the x-rays of the ray beam, respectively measured from the focus of the x-ray radiator to the point of impact on the diaphragm plate. To prevent disadvantageous edge effects in the gating, U.S. Pat. No. 6,396,902 an x-ray collimator is specified in which a number of slits of different but respectively constant width are introduced in a carrier or base body, whereby the carrier body is curved such that the gating slits are also curved. By the curvature of the slits, it should be ensured that a ray beam (dose profile) exactly rectangular in cross section is gated on the x-ray detector.

For different examination methods, in order to be able to operate with different numbers of active detector rows or with an x-ray beam gated at different widths in the direction of the patient axis, given the x-ray collimator known from U.S. Pat. No. 6,396,902 the entire support body produced from x-ray-absorbing material must be moved. According to this disclosure, this occurs by rotation of the bearing body, which is why the support body is also curved around a second axis (shell-shape). In order to also be able to bring another diaphragm slit into the matching position, the rotation axis would have to be located at the height of the focus of the x-ray radiator. This at best possible with very large mechanical effort.

Alternatively, the rotated support body would have to be readjusted into the correct position via a shifting movement, which is likewise very elaborate.

Moreover, the production of a support body curved around two axes is likewise connected with large expenditure, because this must also still be produced from x-ray-absorbing material, meaning from a material with a high atomic number. A further disadvantage of the x-ray collimator known from U.S. Pat. No. 6,396,902 is its large structural volume.

SUMMARY OF THE INVENTION

An object of the present invention is to provide a gating device which can be produced with less expenditure, which exhibits a small space requirement and which nevertheless allows a gating adapted to the geometry of an, if applicable, associated x-ray detector. A computed tomography apparatus should also be specified for this purpose.

This object is achieved in accordance with the invention by a gating device of the type described above but wherein the absorber element is shaped such that the slit, considered in the slit longitudinal direction, has a first middle region of constant slit width and, on each side of the middle region, one further region with the slit width linearly increasing in the slit longitudinal direction, and wherein the adjustment device generates a parallelogram-like relative movement between the absorber elements.

The inventive gating device has the advantage that the absorber element does not or the absorber elements do not necessarily have to exhibit a curved (for example banana-like) shape in order to, for example, achieve a rectangular gating. Rather, the slit can lie in one plane and likewise does not have to be curved towards a third dimension. The absorber element is or the absorber elements are preferably flat or essentially flat, for example disc-shaped or rod-shaped. The gating device can thus be produced simply and with a saving of space.

Considered in the slit longitudinal direction, in particular the first region is centrally arranged, and a further region with slit width varying in the slit longitudinal direction is present on each side of the central region.

The absorber elements are adjustable relative to one another with regard to their separation, such that the x-ray beam can be variably delimited.

In the case of same-shape absorber elements, these preferably lie mirror-symmetrically opposite one another, such that sections of the absorber elements matching one another lie opposite one another with the same slit width variation ("same slit width") with regard to an identical reference point.

The gating device can be particularly simply produced in an advantageous manner from individually manufacturable (if applicable identical or similar) absorber elements.

The adjustment device acts on the absorber elements such that the absorber elements can move perpendicularly or at an angle to the slit longitudinal direction. From this, the special advantage results that the slit width is continuously or freely selectable between the curved absorber elements or diaphragm jaws, and thus the slice thickness adjustable at a computed tomography apparatus equipped with the gating device can also assume non-discrete values. Wide detector rows can also be only partially irradiated, and thus slices that are thinner than the width of the detector elements are also possible in a simple manner.

Moreover, a readjustment of the gating device is still also possible given a modification of the focus size occurring during the operation.

Due to the very space-saving parallelogram-like movement of the absorber elements, a movement component parallel to the slit longitudinal direction also occurs in addition to the movement component perpendicular to the slit longitudinal direction, given always-constant parallel alignment of the absorber elements. Such a parallelogram-like movement is in particular specified in DE 42 26 861 C2, especially in claim 1 thereof.

According to a preferred embodiment, the absorber elements can move independent of one another. It is therewith possible to move the absorber elements not only opposite to one another, but also concurrently in the same direction. For example, a diaphragm readjustment is also possible given a variation of the focus position in the diaphragm rays occurring during the operation (focal spot tracking). This means that the entire slice can also be shifted in the z-direction with a constant slice width. Moreover, a dynamic variation of the collimation width is therewith possible, whereby (for example) an unwanted over-radiation at the beginning and at the end of a spiral scan can be reduced, by one of the absorber elements still being closed at the beginning of the scan and is only opened at the beginning of the scan with the beginning of the translatory patient bed movement in the direction of the system axis. The same is true in reverse for the end of the scan.

The adjustment device for each of the absorber elements has a separate adjustment unit, with the adjustment units, for example, fashioned for a linear movement of the appertaining absorber element. Via such a linear movement, it is ensured in an advantageous manner that matching sections of the absorber elements with the same slit width also still lie opposite one another after a relative movement in the direction of the system axis.

With particular advantage, the adjustment units each have a (preferably mutual) linear guide as well as a drive acting on the absorber elements.

The object with regard to the apparatus is achieved in accordance with the invention by a computed tomography apparatus of the type described above, but wherein the gating device of the computed tomography apparatus is fashioned according to the invention. The slit longitudinal direction thereby preferably is perpendicular to the system axis or rotation axis.

Advantages and preferred embodiments as well as variants are applicable to the computed tomography apparatus according to the invention in a manner analogous to that for the gating device according to the invention.

The x-ray detector of the computed tomography apparatus is in particular a matrix-like detector array, for example a multi-row detector or a planar detector.

According to a very particular embodiment of the computed tomography apparatus, the slit width $l=l(\beta)$ varies dependent on the cosine of a fan angle $\beta$, whereby the fan angle $\beta$ is the angle between an eccentric [off-center] ray of the x-ray beam and a central ray.

The variation is in particular described by the following equation:

$$l(\beta)=C/\cos\beta+D,$$

wherein C and D are selectable as constants in the production for the appertaining slit. Functional dependencies approximating this equation, for example a series expansion according to the fan angle $\beta$, are also applicable.

DESCRIPTION OF THE DRAWINGS

FIG. 4 is a schematic illustration of a first exemplary embodiment of the gating device of the computed tomography apparatus of FIG. 1.

FIG. 5 is a schematic illustration of a second exemplary embodiment of the gating device of the computed tomography apparatus of FIG. 1.

FIG. 6 is a schematic illustration of a third exemplary embodiment of the gating device of the computed tomography apparatus of FIG. 1.

FIG. 7 illustrates the gating device of FIGS. 4 and 5 in cross-section.

DESCRIPTION OF THE PREFERRED EMBODIMENTS

Figure 1:
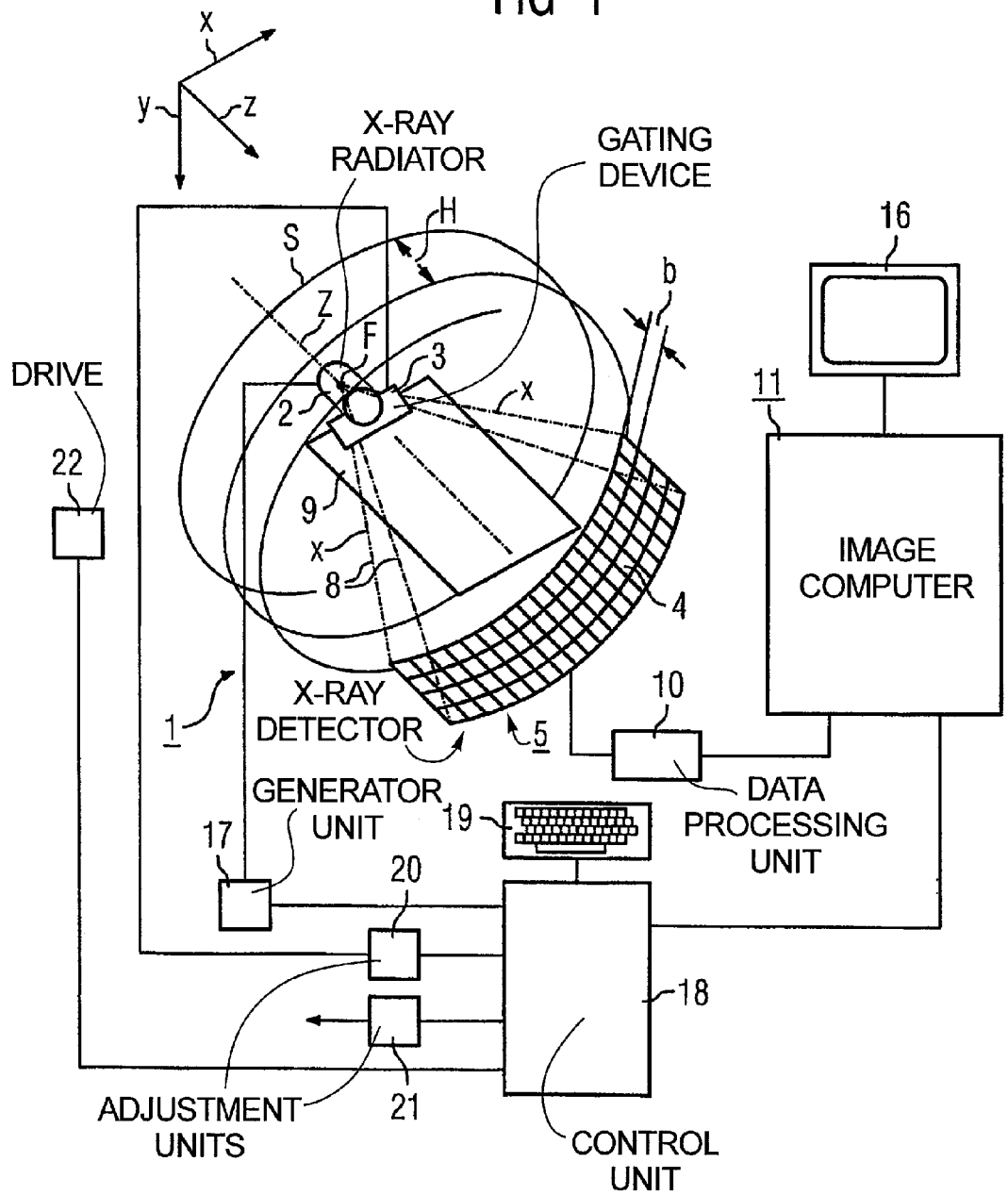
FIG. 1 is a perspective/block diagram illustration of a computed tomography apparatus having a gating device constructed and operating according to the invention.

A CT apparatus of the generation is shown in FIG. 1 in section. Its measurement arrangement includes an x-ray radiator 2 with a gating device 3 positioned in front of it, near the source, and an x-ray detector 5, fashioned as a laminar array of a number of rows and columns of detector elements (one of these is designated with 4 in FIG. 1), with an optional beam diaphragm (not shown) positioned in front of the x-ray detector 5, close to the detector. For clarity, in FIG. 1 only four rows of detector elements 4 are shown; however, the x-ray detector 5 can have further rows of detector elements 4, optionally with different widths b.

The x-ray radiator 2 with the gating device 3 on one side and the x-ray detector 5 with its beam diaphragm on the other side are mounted opposite one another on a rotary frame (gantry) (not shown), such that a pyramidal (viewed in the z-direction: fan-shaped) x-ray beam, emitted by the x-ray radiator 2 in the operation of the CT apparatus 1 and gated by the adjustable gating device 3 (the ray beams of which x-ray beam are designated with 8), strikes the x-ray detector 5. By means of the gating device 3 and, if applicable, by means of the detector-proximate beam diaphragm, a desired cross-section (more precisely: half width) of the x-ray beam is adjusted such that only that region of the x-ray detector 5 is uncovered that should be directly struck by the x-ray beam. In the operating mode illustrated in FIG. 1, there are four rows of detector elements that are designated as active rows. If applicable, further existing rows are covered by the detector-proximal beam diaphragm and are therefore not active. The gating device 3 thereby primarily prevents an unnecessary radiation exposure of the examination subject, in particular a patient, by rays that otherwise do not arrive at the active rows also being kept away from the examination subject or patient.

The rotary frame can be placed in rotation around a system axis Z by means of a drive device 22. The system axis Z runs parallel to the z-axis of a spatial rectangular coordinate system shown in FIG. 1.

The columns of the x-ray detector 5 likewise proceed in the direction of the z-axis, while the rows (whose width b is measured in the direction of the z-axis and is, for example, 1 mm) proceed transversely to the system axis Z, i.e. the z-axis. The x-ray detector 5 is curved or arced around an axis running parallel to the z-axis.

In order to be able to bring the examination subject, for example the patient, into the beam path of the x-ray beam, a support device 9 is provided that can be shifted parallel to the system axis Z, thus in the direction of the z-axis, such that a synchronization exists between the rotation movement of the rotary frame and the translation movement of the support device 9 in the sense that the ratio of translation speed to rotation speed is constant, whereby this ratio is adjustable by a desired value being selected for the infeed h of the bearing device 9 per rotation of the rotary frame.

A volume of an examination subject located on the support device 9 can thus be examined in the course of a volume scanning, with the volume scanning being effected in the form of a spiral scan in the sense that, with rotation of the rotary frame and simultaneous translation of the support device 9, a number of projections is acquired from various projection directions per rotation of the rotary frame. In such a spiral scan, the focus F of the x-ray radiator 2 moves on a spiral track S relative to the support device 9. A sequence scan is also possible as an alternative to this spiral scan.

The measurement data, read out in parallel during the spiral scan from the detector elements 4 of each active row of the x-ray detector 5 and corresponding to the individual projections, are subjected to a digital-analog conversion in a data processing unit 10, and are serialized and transferred to an image computer 11 which shows the result of an image reconstruction on a display unit 16, for example a video monitor.

The x-ray radiator 2, for example an x-ray tube, is supplied with the necessary voltages and currents by a generator unit 17 (optionally likewise rotating). In order to be able to adjust this to the necessary values, a control unit 18 with a keyboard 19 that allows the necessary adjustments is associated with the generator unit 17.

The other operation and control of the CT apparatus 1 also ensues by means of the control unit 18 and the keyboard 19, which is illustrated by the control unit 18 being connected with the image computer 11.

Among other things, the number of the active rows of detector elements 4 (and therewith the position the gating device 3 and of the optional detector-proximate beam diaphragm) can be adjusted, for which purpose the control unit 18 is connected with adjustment units 20 and 21 associated with the gating device 3 and the optional detector-proximate beam diaphragm. Furthermore the rotation time that the rotary frame requires for a complete rotation can be adjusted, which is illustrated by the drive unit 22 associated with the rotary frame being connected with the control unit 18.

Figure 2:
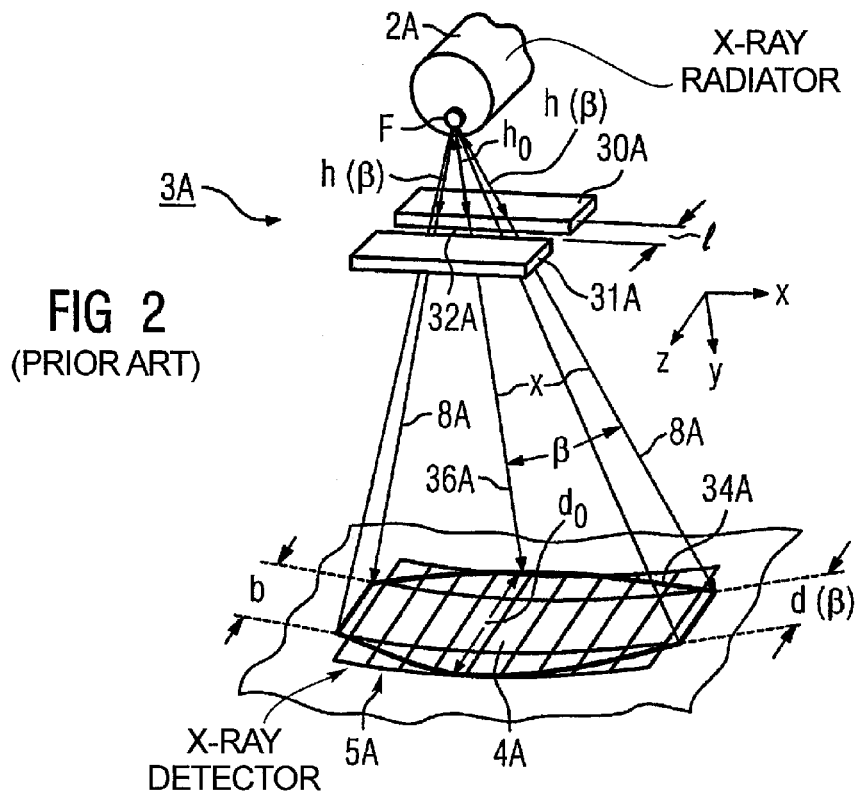
FIG. 2 illustrates a known gating device, wherein the functioning of the gating device is illustrated in perspective.

FIG. 2 shows the gating that results given a known gating device 3A with two separate absorber elements 30A, 31A. Shown is an x-ray beam with edge rays 8A which emanates from a focus F of an x-ray radiator 2A. The x-ray beam can be considered as being composed of many linear rays. There is a fan angle $\beta$ for each ray. The fan angle $\beta$ is measured with regard to a central ray 36A that passes through the gating device 3A perpendicular to a center position. The separation of the central ray 36A from the absorber elements 30A, 31A is designated with $h_0$.

The plane of the gating device 3A is perpendicular to the connecting line from the focus F to the rotation axis Z (see FIG. 1). This connecting line coincides in FIG. 2 with the central ray 36A.

The shown conventional gating device 3A exhibits the same opening or slit width l for all fan angles $\beta$. The following problem results from this: both the edge rays 8A passing the (in FIG. 2) back-side absorber element 30A respectively cover (starting from the focus F) a distance $h(\beta)$ from the absorber element 30A that depends on the fan angle $\beta$:

$$H(\beta) = h_0/\cos\beta > h_0 \qquad [\text{Eq. 1}]$$

In contrast to this, the comparable distance $h_0$ exhibits a lower value given the indicated central ray 36A than given the edge rays 8A. The same is correspondingly true for the edge rays on the opposite side of the slit 32A. The result is that an x-ray beam whose outer contour 34A is not rectangular is gated on the x-ray detector 5A with its individual detector elements 4A in cross-section. In order to fully illuminate all detector elements 4A of the detector row (with its width b) illuminated here, the outer contour 34A must be set such that its width $d(\beta)$ at the edge approximately corresponds to the width b of the detector row. As a result of the different distances $h(\beta) \neq h_0$, a larger width $d_0$ of the outer contour 34A of the x-ray beam then results in the middle of the detector row. The portion of the x-ray beam occurring in this barrel-shaped region (here shown exaggerated, but nevertheless disturbing with regard to the radiation dose) is ultimately not used.

Resulting from the ray set for the gated width $d(\beta)$ for an eccentric fan angle $\beta$ is $$d(\beta) = x \cdot l/h(\beta) \qquad [\text{Eq. 2}]$$

and, with equation 1:

$$d(\beta) = x \cdot l \cdot \cos\beta/h_0 \qquad [\text{Eq. 3}]$$

In the equations, x stands for the focus-detector separation. Due to the curvature of the detector 5a (see also FIG. 1), x is just as large for an edge ray 8A as for the central ray 36A. $h_0$ can also be understood as the difference of the distance focus-rotation axis and the distance diaphragm-rotation center and is typically 200 mm.

Figure 3:
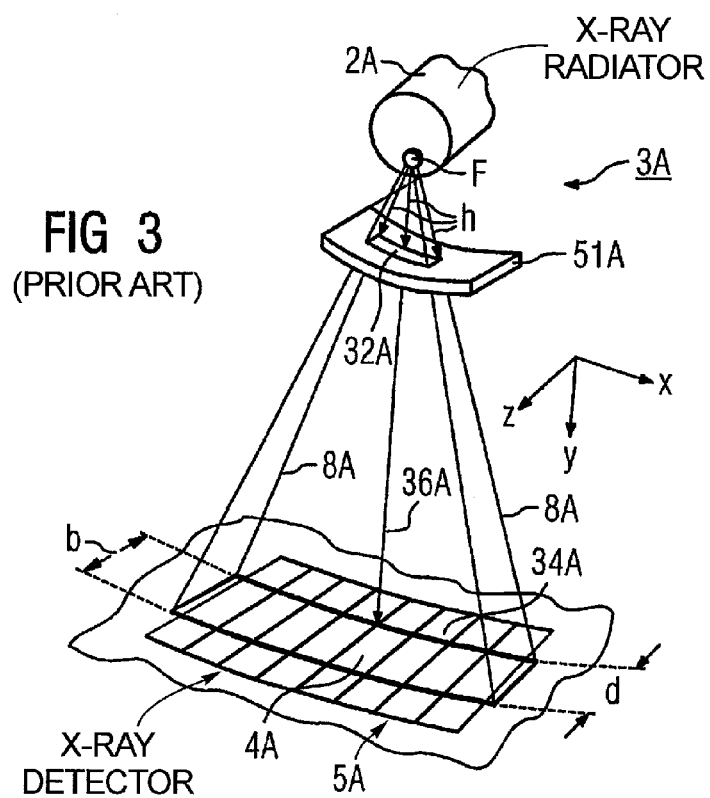
FIG. 3 illustrates a further known gating device.

A further known gating device 3A of a CT apparatus is illustrated in FIG. 3 in schematic representation and perspective view. The gating device 3A comprises a curved absorber element 51A in which is formed a slit 32A that can pass the x-rays starting from the focus F of the x-ray radiator 2A. The absorber element 51A is curved in the shape of a circular arc, whereby the middle point of the circular arc lies in the focus F of the x-ray radiator 2A. With regard to the problem shown with equation 1, it should thereby be ensured that the separation, of both of the edge rays 8A from a central ray 36A measured from the focus F to the absorber element 51A, exhibits the same value h. It should thereby be achieved that the x-ray beam gated on the curved x-ray detector 5A exhibits in cross-section a rectangular outer contour 34A whose constant width d can be adapted to the width b of one or more detector rows.

A further known gating device 3 is shown in FIG. 4 in a schematic representation. The geometry—in particular also with regard to the focus-detector distance x—is largely identical with that of FIG. 2, so the same reference symbols are used.

The absorber elements 30, 31 (produced from heavy metal, for example from tungsten or/and from tantalum) can move or travel independently of one another, in particular oppositely from each other or together with each other, which is indicated by corresponding double arrows 40, 41 in FIG. 4. The absorber elements 30, 31 are shaped, i.e. exhibit on the slit-side a curved outer contour, such that the slit 32 exhibits a slit width t varying in the slit longitudinal direction 42 and increasing towards the slit ends. The absorber elements 30, 31 are correspondingly contoured to their slit-demarcating edges 43 and 44.

The invention proceeds from the consideration that the problem resulting from equation 1 is to be solved starting from equation 3, in that the gated width d(β) is set as a constant: d(β)=d, and then equation 3 is solved according to a slit width l=l(β) assumed to be varying with the fan angle β:

$$l(\beta)=d\cdot h_0/(x\cdot\cos\beta) \quad [\text{Eq. 4}]$$

The slit width l=l(β) this generally varies according to $$l(\beta)=C/\cos\beta+D=C\cdot\sec\beta+D \quad [\text{Eq. 5}]$$

with the fan angle β, whereby C and D apply for the appertaining slit 32 as constants independent of the fan angle β. The slit-demarcating edges 43 and 44 are rounded.

For angles that are not too large, a curve progression approximated according to a series expansion is also applicable:

$$l(\beta)=E+F\cdot\beta^2 \quad [\text{Eq. 6}]$$

whereby E and F are selectable as constants for the appertaining slit 32.

A gating device 3 according to the invention according to a second exemplary embodiment is shown in FIG. 5, as can be installed in the CT apparatus 1 of FIG. 1. In contrast to the exemplary embodiment of FIG. 4, the slit-demarcating edges 43A and 44A of the absorber elements 30, 31 are not curved, but are composed of a number of straight sections. The absorber elements 30, 31 thus exhibit an outer contour polygonally approximating a curve. In a middle first region 45 of approximately 50 mm in length, the slit width l is constant. In each further region 46, 47 (length approximately 75 mm) adjacent on both sides of the first region 45, the slit width l increases linearly towards the ends. The increase Δl of the slit width l is, for example, 0.4 mm.

The embodiment of the gating device 3 according to FIG. 5 is in the case of an adjustment device that generates a parallelogram-like relative movement between the absorber elements 30, 31 to modify the diaphragm opening. Namely, it has been shown that the movement also occurring (among other things) in the x-direction in the parallelogram-like movement, which movement in the x-direction leads to a displacement of the centers of the absorber elements 30, 31, has particularly little effect given a gating device 3 executed with three regions 45, 46, 47, in particular in that errors with regard to this are corrected to the largest possible extent via introduction of calibration implemented at the beginning of a measurement.

A further gating device 3 is shown in FIG. 6, as can likewise be installed into the CT apparatus 1 of FIG. 1. Only a single, one-piece or one-part, plate- or disc-like absorber element 51 is present, having a number of slits 52, 53, 54, 55, 56, 57 with average slit widths differing from one another. The slits 52, 53, 54, 55, 56, 57 are aligned parallel in the slit longitudinal direction 42 and exhibit a slit width l varying in the longitudinal direction 42. The length L of the absorber element 51, measured in the z-direction, is approximately 70 mm; its width B, measured in the x-direction, approximately 200 mm. For better representation of he contoured openings, the absorber element 51 is thus not shown with a uniform scale in FIG. 6. The absorber element 51 can be linearly shifted in the z-direction, thus perpendicular to the slit longitudinal direction 42, which is indicated by the double arrow 59. Suitable adjustment means including a drive unit 60 and a guide element 61 are only schematically indicated.

The gating device 3 of FIGS. 4 and 5 is explained again in FIG. 7 in a cross-section representation in the z-direction. Therein it is in particular visible that the absorber elements 30, 31 are slightly displaced relative to one another in the height direction y, essentially corresponding to the direction of the radiated x-ray beam, in order to achieve an overlapping of the absorber elements 30, 31 necessary for a complete closure of the gating device 3.

Moreover, in FIG. 7 it can be seen that a first drive 63 can be provided as an adjustment device 61 for the absorber element 30 and a separate drive means 67 can be provided for the other absorber element 31 the drives 63 and 67 act on the absorber elements 30, 31 to move them along the common linear guide 65 via toothed belts and/or gears. The adjustment device 61 is connected with the control unit 18. The adjustment device 61 can alternatively drive both absorber elements 30, 31 with a common motor.

Although modifications and changes may be suggested by those skilled in the art, it is the invention of the inventors to embody within the patent warranted heron all changes and modifications as reasonably and properly come within the scope of their contribution to the art.

The invention claimed is:

1. A gating device to delimit an x-ray beam, said gating device comprising:

a device housing;

first and second absorber elements mounted in said device housing opposite each other;

an adjustment device connected to said first and second absorber elements for moving said absorber elements relative to each other to set a spacing between said first and second absorber elements forming a slit for passage of an x-ray beam therethrough;

each of said absorber elements having an absorber element edge shaped to give said slit a slit width that varies in a longitudinal direction of the slit, said slit width increasing outwardly, from a central position, toward respectively opposite ends of said slit, each slit edge, in said longitudinal direction of said slit, having a middle region producing a uniform width of said slit, and further regions respectively disposed on opposite sides of said middle region that produce a linearly increasing slit width in said longitudinal direction of said slit; and said adjustment device producing a parallelogram-like relative movement between said absorber elements.

2. A gating device as claimed in claim 1 wherein each absorber comprises an absorber element body formed by a flat plate having said absorber element edge.

3. A computed tomography apparatus comprising:

an x-ray radiator that emits an x-ray beam;

an x-ray detector disposed in a path of said x-ray beam for detecting x-rays in said x-ray beam, said x-ray radiator and said radiation detector being rotatable around a system axis; and a gating device disposed in front of and proximate to said x-ray radiator, said gating device comprising a device housing, first and second absorber elements mounted in said device housing opposite each other, an adjustment device connected to said first and second absorber elements for moving said absorber elements relative to each other to set a spacing between said first and second absorber elements forming a slit for passage of an x-ray beam therethrough, with each of said absorber elements having an absorber element edge shaped to give said slit a slit width that varies in a longitudinal direction of the slit, said slit width increasing outwardly, from a central position, toward respectively opposite ends of said slit, each slit edge, in said longitudinal direction of said slit, having a middle region producing a uniform width of said slit, and further regions respectively disposed on opposite sides of said middle region that produce a linearly increasing slit width in said longitudinal direction of said slit, and said adjustment device producing a parallelogram-like relative movement between said absorber elements.

4. A computed tomography apparatus as claimed in claim 3 wherein said x-ray beam exhibits a fan angle $\beta$ between a central ray of said x-ray beam and an edge ray of said x-ray beam, and wherein the respective edges of said first and second absorber elements, in combination, produce a width of said slit that approximately varies dependent on $\cos \beta$.

5. A computed tomography apparatus as claimed in claim 3 wherein said x-ray beam exhibits a fan angle $\beta$ between a central ray of said x-ray beam and an edge ray of said x-ray beam, and wherein the respective edges of first and second absorber elements, in combination, produce a width of said slit that approximately varies according to $$l(\beta)=C/\cos\beta+D,$$

wherein C and D represent respective constants for said slit.

* * * * *